United States Patent
Coleman et al.

(10) Patent No.: US 10,421,795 B2
(45) Date of Patent: Sep. 24, 2019

(54) PROCESS FOR PURIFYING INSULIN AND ANALOGUES THEREOF

(71) Applicants: Merck Sharp & Dohme Corp., Rahway, NJ (US); Michael P. Coleman, Louisville, CO (US); Allison D. Ortigosa, McGaheysville, VA (US); Mark C. Sleevi, Longmont, CO (US); Kartoa Chow, Oakland Gardens, NY (US)

(72) Inventors: Michael P. Coleman, Louisville, CO (US); Allison D. Ortigosa, McGaheysville, VA (US); Mark C. Sleevi, Longmont, CO (US); Kartoa Chow, Oakland Gardens, NY (US)

(73) Assignee: Merck Sharp & Dohme Corp., Rahway, NJ (US)

(*) Notice: Subject to any disclaimer, the term of this patent is extended or adjusted under 35 U.S.C. 154(b) by 256 days.

(21) Appl. No.: 14/652,494

(22) PCT Filed: Dec. 12, 2013

(86) PCT No.: PCT/US2013/074570
§ 371 (c)(1),
(2) Date: Jun. 16, 2015

(87) PCT Pub. No.: WO2014/099577
PCT Pub. Date: Jun. 26, 2014

(65) Prior Publication Data
US 2015/0329612 A1    Nov. 19, 2015

Related U.S. Application Data

(60) Provisional application No. 61/738,015, filed on Dec. 17, 2012.

(51) Int. Cl.
*C07K 14/62* (2006.01)
*A61K 38/00* (2006.01)

(52) U.S. Cl.
CPC .............. *C07K 14/62* (2013.01); *A61K 38/00* (2013.01)

(58) Field of Classification Search
CPC . A61K 30/00; C07K 14/62; C12N 2015/8518
See application file for complete search history.

(56) References Cited

U.S. PATENT DOCUMENTS

| | | | |
|---|---|---|---|
| 5,101,013 A * | 3/1992 | Dorschug | C07K 1/18 530/303 |
| 5,621,073 A | 4/1997 | Dickhardt et al. | |
| 5,700,662 A | 12/1997 | Chance et al. | |
| 5,977,297 A * | 11/1999 | Obermeier | C07K 14/62 530/300 |
| 6,451,987 B1 * | 9/2002 | Staby | C07K 1/18 210/656 |
| 6,531,448 B1 | 3/2003 | Brader et al. | |
| 6,710,167 B1 * | 3/2004 | Sievers | C07K 14/62 530/303 |
| 6,870,034 B2 * | 3/2005 | Breece | C07K 1/22 436/824 |
| 7,803,763 B2 * | 9/2010 | Thurow | C07K 14/62 514/5.9 |
| 7,968,679 B2 | 6/2011 | Sleevi et al. | |
| 8,048,854 B2 | 11/2011 | Habermann et al. | |
| 2004/0029164 A1 | 2/2004 | Ransohoff et al. | |
| 2004/0102615 A1 | 5/2004 | Berna et al. | |
| 2006/0183669 A1 * | 8/2006 | Hansen | C07K 1/18 514/6.3 |
| 2009/0312236 A1 | 12/2009 | Beals et al. | |
| 2011/0065901 A1 | 3/2011 | Soice et al. | |
| 2012/0058513 A1 * | 3/2012 | Lazaryev | C07K 14/62 435/69.4 |
| 2012/0149878 A1 | 6/2012 | Gillespie et al. | |

FOREIGN PATENT DOCUMENTS

| | | |
|---|---|---|
| AU | 3172477 | 6/1979 |
| GB | 2173503 A | 10/1986 |
| WO | 2011090719 A2 | 7/2011 |

OTHER PUBLICATIONS

Basic Guide to Protein Chromatography/Purification, San Diego State University, 2006.*
GE Healthcare Data File 18-1107-12 AB product information for Source 30 S, Aug. 2007.*
Insaidoo, et al., Targeted Purification Development Enabled by Computational Biophysical Modeling, Biotechnol. Prog. vol. 31, No. 1 pp. 154-164.
"Insulin glargine—Wikipedia", Nov. 10, 2012, retrieved on Apr. 23, 2019 from https://en.wikipedia.org/w/index.php?title=Insulinglargine&oldid=522308377.
Examiners Interview held on Mar. 5, 2019 for U.S. Appl. No. 14/652,494.
GE Healthcare, Capto SP ImpRes, Capto Q ImpRes, Ion Exchange Chromatography, 2011, 1-12, Data File 28-9837-63 AB.
GE Healthcare, Ion exchange columns and media, Selection Guide, 2008, 1-8, 18-1127-31 AH.
GE Healthcare, Life Sciences, High-throughput process development and scale-up of an intermediate purification step for recombinate insulin, Process Development, 2012, 1-8, Application Note 29-0018-56 AA.
Notice of Opposition of EP2931301, Merck Sharp & Dohme Corp., dated Apr. 29, 2019, 32 pages.
Pall Life Sciences, Q, S, Deae, CM Ceramic HyperD F, Ion Exchange Sorbents, Product Note, 2011, 1-6, USD 2774.

(Continued)

*Primary Examiner* — Karlheinz R. Skowronek
*Assistant Examiner* — Joseph Fischer
(74) *Attorney, Agent, or Firm* — John David Reilly; Laura M. Ginkel (57) ABSTRACT

A process is described for purifying insulin and insulin analogs that comprises high-pressure liquid chromatography with an acidic cation exchange medium performed under low to moderate pressure at an elevated temperature.

2 Claims, 1 Drawing Sheet
Specification includes a Sequence Listing.

(56) References Cited

OTHER PUBLICATIONS

Staby, Arne, Comparison of chromatographic ion-exchange resins III. Strong cation-exchange resins, Journal of Chromatography A, 2004, 85-97, 1034.
Tosoh Bioscience, Ion Exchange Chromatography, Manual, 15-28.
"Screenshot Wayback Machine", Aug. 21, 2006, retrieved on Mar. 19, 2019 from https://web.archive.org/web/20060821204727/http://wolfson.huji.ac.il/purification/PDF/IonExchange/TOSOHJEC.pdf.

* cited by examiner

PROCESS FOR PURIFYING INSULIN AND ANALOGUES THEREOF

This application claims priority to International Application No. PCT/US2013/074570, filed 12 Dec. 2013 and which claims benefit of U.S. Provisional Application No. 61/738,015 filed 17 Dec. 2012, the content of each of which is hereby incorporated by reference in its entirety.

REFERENCE TO SEQUENCE LISTING SUBMITTED ELECTRONICALLY

The sequence listing of the present application is submitted electronically via EFS-Web as an ASCII formatted sequence listing with a file name "MRLDOB00077-SE-QTXT-16JUN2015.txt", creation date of Jun. 16, 2015 and a size of 2 KB. This sequence listing submitted via EFS-Web is part of the specification and is herein incorporated by reference in its entirety.

BACKGROUND OF THE INVENTION

(1) Field of the Invention

The present invention relates to a process for purifying insulin and insulin analogues comprising liquid chromatography with an acidic cation exchange medium performed under low to moderate pressure at an elevated temperature.

(2) Description of Related Art

Recombinant production of insulin and insulin analogs in genetically modified microbial or yeast host cells entails expression of the insulin or insulin analog in the host cell as a single-chain precursor insulin molecule comprising three polypeptide domains (A-chain, C-chain, B-chain), as in native pre-insulins, along with the addition of a fusion peptide at the N-terminus whose function is to allow the correct N-terminal sequence of the insulin to be obtained during its synthesis in the host cell.

In the microbial host *E. coli*, the single-chain precursor insulin molecule is sequestered in inclusion bodies consisting of mostly of incorrectly folded single-chain precursor molecules. To produce recombinant insulin, the inclusion bodies are extracted from the cell, washed, and the single-chain precursor molecule is solubilized, refolded, and then purified by at least one chromatographic step. The refolded, single-chain precursor molecule is then further processed into a heterodimer insulin molecule by the concurrent removal of the C-chain and the N-terminus fusion peptide by enzymatic digestion. The insulin heterodimer comprises the A-chain and B-chain polypeptides linked together by three disulfide bridges. In subsequent purification steps including ion-exchange chromatography and reverse phase HPLC, the insulin heterodimer is purified away from digestion byproducts to yield a highly purified product. The purified product may be formulated in a zinc and m-cresol (preservative) containing buffer to provide the insulin product.

Methods for isolating inclusion bodies, refolding and enzymatically digesting precursor insulin molecules to produce insulin heterodimers have been disclosed U.S. Pat. Nos. 5,663,291; 5,986,048; 6,380,355, and 5,473,049. Ion-exchange chromatography methods for purifying insulin heterodimers from digestion byproducts have been disclosed in U.S. Pat. No. 5,101,013, which discloses cation-exchange chromatography on strongly acidic ion exchangers under atmospheric or medium pressure and elution by means of aqueous alkanol with only a relatively small amount of alkanol to purify insulin heterodimers; and, U.S. Pat. No. 5,977,297, which discloses high-pressure cation-exchange chromatography on pressure-stable acidic cation exchangers under a pressure of about 1.1 MPa (11 bar) to about 40 MPa (400 bar) to purify insulin heterodimers. Further purification of the insulin heterodimer has been described in U.S. Pat. Nos. 6,710,167 and 5,621,073.

While there are methods available for purifying insulin heterodimers, there remains a need for alternative methods for purifying insulin heterodimers and analogues thereof.

BRIEF SUMMARY OF THE INVENTION

In an effort to provide additional processes for obtaining insulin or insulin analog heterodimers from enzymatic cleavage reactions, we have found that insulin and insulin heterodimers can be purified from other byproducts of the enzymatic digestion by chromatography of the insulin or insulin analog heterodimers on temperature-stable acidic cation exchangers under a pressure of about 0.276 MPa (40 psi or 2.7 bar). The method is capable of yielding a composition of insulin or insulin analogue heterodimers with a purity of about 90% or greater and a yield of 65 to 85% or more as determined by high pressure liquid chromatography (HPLC).

Therefore, the present invention provides a process for isolating insulin or insulin analogue by chromatography comprising the steps of: (a) obtaining a column comprising an acidic cation exchange material; (b) loading the column with a sample solution including an insulin or insulin analogue; (c) performing chromatography; and (d) eluting the insulin or insulin analogue from the column with an eluting solution; the process being performed under a column differential pressure of less than 1.1 MPa and at an outlet temperature greater than about 20° C., 30° C., or 40° C. In particular aspects, the outlet temperature is within the range 37° C. and 47° C. inclusive, about 42° C. or more, within the range 42° C. to 47° C. inclusive, or about 42° C.

In a further aspect of the process, the eluting step is performed using an eluting solution comprising an aqueous mixture which comprises from about 10 to about 50 percent by volume of a water miscible organic modifier. In a further aspect, the eluting step is performed using an eluting solution comprising an aqueous mixture which comprises from about 25 to about 35 percent by volume of a water miscible organic modifier. In particular aspects, the water miscible organic modifier is hexylene glycol.

In particular aspects, the acidic cation exchange material is a weak cation exchanger comprising carboxy or carboxymethyl functional groups. In particular aspects, the acidic cation exchange material is a strong cation exchanger comprising sulfonic acid functional groups. In a further aspect of the process, the acidic cation exchange material is temperature-stable, which in particular aspects may comprise a high-capacity hydrogel polymerized within the pores of a rigid ceramic bead and cross-linked to sulfo groups on the bead. Thus, the temperature-stable acidic cation exchange material comprises a high-capacity hydrogel polymerized within the pores of rigid ceramic beads and cross-linked to sulfo groups on the beads. In particular aspects, the hydrogel comprises carboxy or carboxymethyl functional groups, or sulfonic acid functional groups.

In a further aspect of the process, the loading step is performed with a sample solution comprising from about 3.0 to about 26.0 g of protein per liter in a solution comprising a water miscible organic modifier. In a further aspect, the sample solution comprises from 10 to about 50 percent by volume of a water miscible organic modifier. In a further aspect, the loading step is performed using an aqueous mixture which comprises from about 25 to about 35 percent by volume of a water miscible organic modifier. In particular aspects, the water miscible organic modifier is hexylene glycol.

In a further aspect of the process, the elution of the insulin is isocratic.

In a further aspect of the process, the differential pressure is less than 1.0 MPa, or less than 0.5 MPa, or about 0.276 MPa.

In a further aspect of the process, performing the chromatography includes a step of washing the column with a first wash solution comprises a concentration of mineral salt of about 10 mM to about 20 mM, which in particular aspects may be NaCl. In a further aspect, the first wash solution comprises from 10 to about 50 percent by volume of a water miscible organic modifier. In a further aspect, the first wash solution comprises from about 25 to about 35 percent by volume of a water miscible organic modifier. In particular aspects, the water miscible organic modifier is hexylene glycol.

In a further aspect of the process, performing the chromatography includes an optional step of washing the column with a second wash solution comprising a mineral salt at a concentration that is greater than the mineral salt concentration in the first wash solution and less than a mineral salt concentration capable of eluting the insulin or insulin analogue from the column prior to eluting the insulin or insulin analogue. In particular aspects, the mineral salt may be NaCl. In a further aspect, the second wash solution comprises from 10 to about 50 percent by volume of a water miscible organic modifier. In a further aspect, the second wash solution comprises from about 25 to about 35 percent by volume of a water miscible organic modifier. In particular aspects, the water miscible organic modifier is hexylene glycol.

In a further aspect of the process, the eluting solution comprises a mineral salt at a concentration capable of eluting the insulin or insulin analogue from the column. In particular aspects, the mineral salt may be NaCl.

In further aspects of the process, the insulin is native human, porcine, or bovine insulin. In further aspects, the insulin analogue is an acid-stable insulin analogue, which is stable and soluble in acidic or weakly acidic solutions and insoluble or partially insoluble at physiological pH, or a pI-shifted insulin analogue in which the pI of the insulin analogue is less than or greater than the pI of native human insulin. The pI of native insulin is 5.4 to 5.6 thus a pI shifted insulin analogue has a pI greater than 5.6 or less than 5.4. In particular aspects the insulin analogue has a pI from between 5.8 to 8.0. An acid-stable insulin analogue such as insulin glargine has a pI of about 6.7 to 7.0. In a further aspect, the insulin analogue is insulin glargine, insulin aspart, insulin glulisine, or insulin lispro. For chromatography of acid-stable insulins a weak cation material may be used and for chromatography for insulins with a pI similar to that of native insulin, a strong cation exchange material may be used.

In general, for insulin analogues with a pI greater than the pI of native insulin, the cation exchanger is a weak cation exchange and for insulin analogues with a pI similar to that of native insulin, the cation exchanger is a strong cation exchanger.

The present invention further provides a process for isolating an acid-stable insulin analogue by chromatography comprising the steps of (a) obtaining a column comprising an acidic cation exchange material; (b) loading the column with a sample solution including the acid-stable insulin analogue; (c) washing the column with a first wash solution comprising a concentration of mineral salt of about 10 to 25 mM; (d) washing the column with a second wash solution comprising a concentration of mineral salt greater than the concentration of mineral salt in the first wash solution and less than the concentration of mineral salt capable of eluting the acid-stable insulin analogue from the column; and (e) eluting the insulin analogue from the column with an eluting solution comprising the concentration of mineral salt capable of eluting the acid-stable insulin analogue from the column; the process being performed under a column differential pressure of less than 1.1 MPa and at an outlet temperature greater than about 20° C., 30° C., or 40° C. In particular aspects, the outlet temperature is within the range 37° C. and 47° C. inclusive, about 42° C. or more, within the range 42° C. to 47° C. inclusive, or about 42° C.

In a further aspect of the process, the eluting step is performed using an eluting solution comprising an aqueous mixture which comprises from about 10 to about 50 percent by volume of a water miscible organic modifier. In a further aspect, the eluting step is performed using an aqueous mixture which comprises from about 25 to about 35 percent by volume of a water miscible organic modifier. In particular aspects, the water miscible organic modifier is hexylene glycol.

In further aspects, the acidic cation exchange material is a weak cation exchanger comprising carboxy or carboxymethyl functional groups. In a further aspect of the process, the acidic cation exchange material is temperature-stable, which in particular aspects may comprise a high-capacity hydrogel polymerized within the pores of a rigid ceramic bead and cross-linked to sulfo groups on the bead. Thus, in particular aspects, the temperature-stable acidic cation exchange material comprises a high-capacity hydrogel polymerized within the pores of rigid ceramic beads and cross-linked to sulfo groups on the beads, wherein the hydrogel comprises carboxy or carboxymethyl functional groups.

In a further aspect of the process, the loading step is performed with a sample solution comprising from about 3.0 to about 26.0 g of protein per liter in a solution comprising a water miscible organic modifier. In a further aspect, the sample solution comprises from 10 to about 50 percent by volume of a solution comprising a water miscible organic modifier. In a further aspect, the loading step is performed using an aqueous mixture which comprises from about 25 to about 35 percent by volume of a water miscible organic modifier. In particular aspects, the water miscible organic modifier is hexylene glycol. In particular aspects, the sample solution has a PH of about pH 3.5 to 5.1.

In a further aspect of the process, the elution of the insulin is isocratic.

In a further aspect of the process, the differential pressure is less than 1.0 MPa, or less than 0.5 MPa, or about 0.276 MPa.

In a further aspect of the process, the first wash solution comprises a concentration of mineral salt of about 18 mM to about 22 mM, which in particular aspects may be NaCl. In a particular aspect, the first wash solution comprises a concentration of mineral salt of about 20 mM, which in particular aspects may be NaCl. In a further aspect, the first wash solution comprises from 10 to about 50 percent by volume of a water miscible organic modifier. In a further aspect, the first wash solution comprises from about 25 to about 35 percent by volume of a water miscible organic modifier. In a further aspect, the first wash solution comprises about 30 percent by volume of a water miscible organic modifier. In particular aspects, the water miscible organic modifier is hexylene glycol. In particular aspects, the column is washed with about 5 to 20 volumes of the wash solution.

In a further aspect, the second wash solution comprises a concentration of mineral salt of about 35 mM to 39 mM of a mineral salt, which in particular aspects may be NaCl. In a further aspect, the concentration of mineral salt is about 37 mM, which in particular aspects may be NaCl. In a further aspect, the column is washed with about 15 to 25 volumes of the second wash solution.

In further aspects of the process, the eluting solution comprises a concentration of mineral salt of about 80 to 100 mM, which in particular aspects may be NaCl. In further aspects of the process, the eluting solution comprises a concentration of mineral salt of about 93 to 97 mM, which in particular aspects may be NaCl. In further aspects of the process, the eluting solution comprises a concentration of mineral salt of about 95 mM, which in particular aspects may be NaCl. In particular aspects, the acid-stable insulin analogue is eluted from the column with about 20 column volumes of the eluting solution.

In further aspects of the process, the acid-stable insulin analogue has a residence time on the column of about 4 to 15 minutes. In particular aspects, the residence time is about 0.238 to about 0.263 minutes per centimeter packed column bed height or about 0.250 minutes per centimeter of packed column bed height.

In further aspects of the process, the acid-stable insulin analogue has a pI between 5.8 and 8.0. In particular aspects, the acid-stable insulin analogue is insulin glargine.

In a further aspect, process is provided for isolating insulin glargine by chromatography comprising the steps of: (a) obtaining a column comprising an acidic cation exchange material; (b) loading the column with a sample solution including the insulin glargine; (c) washing the column with a first wash solution comprising about 18 to 22 mM of NaCl; (d) washing the column with a second wash solution comprising about 35 to 39 mM of NaCl; and (e) eluting the insulin glargine from the column with an eluting solution comprising about 93 to 97 mM of NaCl; the process being performed under a column differential pressure of less than 1.1 MPa and at an outlet temperature greater than about 20° C., 30° C., or 40° C. In particular aspects, the outlet temperature is within the range 37° C. and 47° C. inclusive, about 42° C. or more, within the range 42° C. to 47° C. inclusive, or about 42° C.

In further aspects of the process, the first and second wash steps and the eluting steps are performed using a first, second, and eluting solution, each comprising an aqueous mixture having about 25 to about 35 percent by volume of a water miscible organic modifier, which in a further aspect, the first and second wash steps and the eluting step are performed using an aqueous mixture which comprises from about 30 percent by volume of a water miscible organic modifier. In a further aspect of the process, the water miscible organic modifier is hexylene glycol.

In a further aspect of the process, the first wash solution comprises about 20 mM NaCl, the second wash solution comprises about 37 mM NaCl, and the eluting solution comprises about 80 to 100 mM, 93 to 97 mM, or 95 mM NaCl.

In further aspects, the acidic cation exchange material is a weak cation exchanger comprising carboxy or carboxymethyl functional groups. In a further aspect of the process, the acidic cation exchange material is temperature-stable, which in particular aspects may comprise a high-capacity hydrogel polymerized within the pores of a rigid ceramic bead and cross-linked to sulfo groups on the bead. Thus, in particular aspects, the temperature-stable acidic cation exchange material comprises a high-capacity hydrogel polymerized within the pores of rigid ceramic beads and cross-linked to sulfo groups on the beads, wherein the hydrogel comprises carboxy or carboxymethyl functional groups.

In a further aspect of the process, the loading step is performed with a sample solution comprising from about 3.0 to about 26.0 g of protein per liter in a solution comprising a water miscible organic modifier. In a further aspect, the water miscible organic modifier is hexylene glycol.

In a further aspect of the process, the elution of the insulin glargine is isocratic.

In a further aspect of the process, the first wash, the second wash, and the elution are each performed with about 10 to 20 column volumes.

In a further aspect of the process, the differential pressure is less than 1.0 MPa. In a further aspect, the differential pressure is less than 0.5 MPa, and in a further aspect, the differential pressure is about 0.276 MPa.

In further aspects of the process, the insulin glargine has a residence time on the column of about 4 to 15 minutes. In particular aspects, the residence time is about 0.238 to about 0.263 minutes per centimeter packed column bed height or about 0.250 minutes per centimeter of packed column bed height.

In the above aspects, the insulin or insulin analogue is obtained from an enzymatic digest of the insulin or insulin analogue.

DEFINITIONS

As used herein, the term "insulin" means the active principle of the pancreas that affects the metabolism of carbohydrates in the animal body and which is of value in the treatment of diabetes mellitus. The term includes synthetic and biotechnologically derived products that are the same as, or similar to, naturally occurring insulins in structure, use, and intended effect and are of value in the treatment of diabetes mellitus.

The term "insulin" or "insulin molecule" is a generic term that designates the 51 amino acid heterodimer comprising the A-chain peptide having the amino acid sequence shown in SEQ ID NO: 1 and the B-chain peptide having the amino acid sequence shown in SEQ ID NO: 2, wherein the cysteine residues a positions 6 and 11 of the A chain are linked in a disulfide bond, the cysteine residues at position 7 of the A chain and position 7 of the B chain are linked in a disulfide bond, and the cysteine residues at position 20 of the A chain and 19 of the B chain are linked in a disulfide bond.

The term "insulin analogue" as used herein includes any heterodimer analogue that comprises one or more modification(s) of the native A-chain peptide and/or B-chain peptide. Modifications include but are not limited to substituting an amino acid for the native amino acid at a position selected from A4, A5, A8, A9, A10, A12, A13, A14, A15, A16, A17, A18, A19, A21, B1, B2, B3, B4, B5, B9, B10, B13, B14, B15, B16, B17, B18, B20, B21, B22, B23, B26, B27, B28, B29, and B30; and/or deleting any or all of positions B1-4 and B26-30. Insulin analogues include molecules having one to 10 amino acids at the N or C terminus of the A-chain peptide and/or B-chain peptide. Insulin analogues further include molecules amidated at the C-terminus of the A-chain peptide and/or B-chain peptide. Examples of insulin analogues include but are not limited to the heterodimer analogues disclosed in published international application WO20100080606, WO2009/099763, and WO2010080609, the disclosures of which are incorporated herein by reference. Insulin glargine (Gly(A21), Arg(B31), Arg(B32)-human insulin: A-chain peptide SEQ ID NO:3; B-chain peptide SEQ ID NO:4), insulin lispro (Lys(B28), Pro(B29)-human insulin: A-chain peptide SEQ ID NO:1; B-chain peptide SEQ ID NO:5, insulin glusiline (Lys(B3), Glu(B29)-human insulin: A-chain peptide SEQ ID NO:1; B-chain peptide SEQ ID NO:6), and insulin detemir (Lys-myristic acid(B29)-human insulin: A-chain peptide SEQ ID NO:1; B-chain peptide SEQ ID NO:2 with B-29 acylated with myristic acid) are examples of commercially available insulin analogues.

The term "insulin analogues" further includes heterodimer polypeptide molecules that have little or no detectable activity at the insulin receptor but which have been modified to include one or more amino acid modifications or substitutions to have an activity at the insulin receptor that has at least 1%, 10%, 50%, 75%, or 90% of the activity at the insulin receptor as compared to native insulin. In particular aspects, the insulin analogue is a partial agonist that has from 2× to 100× less activity at the insulin receptor as does native insulin. In other aspects, the insulin analogue has enhanced activity at the insulin receptor.

BRIEF DESCRIPTION OF THE DRAWINGS

FIG. 1 shows a CEX chromatography gradient profile. Following loading of the insulin sample from an enzymatic digest in buffer A1, the column is washed with A1 buffer (Wash 1) for 20 column volumes. Next, the column is washed with Wash 2 containing an A1/B1 mixture (about 6.5% B1) for 20 column volumes as shown. The insulin sample is eluted with an A1/B1 mixture (about 26% B1) for twenty column volumes as shown. The column is stripped using B1 buffer.

DETAILED DESCRIPTION OF THE INVENTION

Precursor insulin or insulin analogue molecules produced in prokaryote host cells such as *E. coli* or lower eukaryote host cells such as *Saccharomyces cerevisiae* or *Pichia pastoris* are enzymatically cleaved in vitro to remove the connecting peptide joining the B-chain peptide to the A-chain peptide to produce insulin or insulin analogue heterodimers. The enzymatic cleavage of precursor insulin or insulin analogue molecules is using achieved by digestion with trypsin, carboxypeptidase, lysC, or combinations thereof. However, the enzymatic digests introduce impurities such as the three amino acid B-chain truncate (des-Thr), deamidoinsulin, arginine- and diarginine-insulin and insulin ethyl ester. To remove these impurities, the present invention provides a cation exchange process that can be performed in column chromatography format in which during the chromatography the column differential pressure is less than 1.1 MPa and the outlet temperature is about 42° C. or more. In particular aspects, the outlet temperature is within the range 37° C. and 47° C. inclusive, about 42° C. or more, within the range 42° C. to 47° C. inclusive, or about 42° C.

The acidic cation exchange material may be a temperature-stable acid cation exchange material, which in a further still aspect, may be a high-capacity hydrogel polymerized within the pores of a rigid ceramic bead and cross-linked to sulfo groups on the beads, for example, BioSepra CM Ceramic HyperD F ceramic beads comprising a highly substituted hydrogel comprising carboxymethyl functional groups therein (available from Pall Corporation, Port Washington, N.Y.) is a weak cation exchanger whereas BioSepra S Ceramic HyperD F ceramic beads comprising a highly substituted hydrogel comprising sulfonic acid functional groups therein (available from Pall Corporation, Port Washington, N.Y.) is a strong cation exchanger. In other aspects, the temperature-stable acidic cation exchange material may be a copolymer of polystyrene and divinylbenzene, which has been modified with sulfo groups. Thus, acidic cation exchange materials that may be used in the process include but are not limited to BioSepra CM Ceramic HyperD F ceramic beads comprising a highly substituted hydrogel therein, which are available from Pall Corporation, Port Washington, N.Y.; BioSepra CM Ceramic HyperD F ceramic beads comprising a highly substituted hydrogel therein, which are available from Pall Corporation, Port Washington, N.Y.; Source 30S or 15S polystyrene/divinyl benzene polymer resins, which are available from GE Healthcare Life Sciences, Pittsburgh, Pa.; POROS 50 μm resins, which are available from Life Technologies, Carlsbad, Calif.), and MACROPREP 50 μm methacrylate resins, which are available from by Biorad Corp. (Hercules, Calif.).

The acidic cation exchange material may be packed into a column for chromatography using known, conventional methods. In general, the acidic cation exchange material is equilibrated in a strip/storage buffer solution and then packed into a column. After the column is packed with the acidic cation exchange material, the column is briefly flushed with a cleaning solution comprising a base, for example NaOH, as a pre-use sanitization step and then promptly flushed with a pre-equilibration solution followed by the strip/storage solution. The acidic cation exchange material should be exposed to the cleaning solution and the pre-equilibration solution for as little time as possible to reduce downstream pressure issues from occurring during the purification of insulin or insulin analogue.

In general, the eluents (strip/storage solution, pre-equilibration solution, and elution solution) comprise a buffer substance, water, and organic solvents. Suitable buffer substances include phosphates, alkali metal or alkaline earth metal salts, such as potassium acetate, ammonium citrate, sodium citrate, acetate, sulfate or chloride.

The eluents further contain water-miscible organic solvents such as alcohols, ketones, methyl acetate, dioxane, or acetonitrile. Alcohols such as hexylene glycol, n- or iso-propanol, methanol, ethanol, or butanol may be used as the water-miscible organic solvent. The concentration of the water-miscible organic solvent for the chromatography is from about 10 to about 50% by volume, from about 20 to about 40% by volume, or from about 25 to about 35% by volume. The concentration of the buffer substance is from about 1 mM to about 100 mM, about 10 to 50 mM, about 50 mM, or about 20 mM. Further additives include a physiologically tolerated mineral salt such as NaCl and may include one or more organic acids such as formic acid, acetic acid, lactic acid or citric acid, a base, e.g., NaOH, and/or preservatives. The pH of the buffer solution comprising the buffer substance is from about 2.5 to about 5.5. In particular aspects, the pH is about 5.1.

In general, the pre-equilibration solution will comprise a buffer solution; the equilibration solution will comprise a buffer solution, a water-miscible organic solvent, and a mineral salt, for example NaCl; the strip/storage solution will comprise a buffer solution, a water-miscible organic solvent, and an amount of mineral salt; for example NaCl greater than the amount in the equilibration solution and of a concentration sufficient to remove any proteins or impurities bound to the acidic cation exchange material in the column, e.g., about 10 to 25 times, about 12.5 times the amount of mineral salt in the equilibration solution.

Loading the column, chromatography, and elution of the insulin or insulin analogue is achieved using known, conventional technical methods. The loading of the column with a loading solution comprising the insulin or insulin analogue to be purified may have a protein content of about 3.0 to 26.0 grams of insulin or insulin analogue per liter of acidic cation exchange material. In general, the loading of the acidic cation exchange material may be achieved by dissolving the insulin or insulin analogue mixture in a buffer solution similar to the equilibration buffer for the acidic cation exchange material as described herein to provide a sample solution. In particular aspects, the insulin or insulin analogue is provided in a sample solution with a pH of about 3.5 to 5.1, or about 4.2, at a concentration of about 1 to 2 g/L, which may further include a water miscible organic modifier. In particular aspects, the sample solution comprises from 10 to about 50 percent by volume of a solution comprising a water miscible organic modifier. In a further aspect, the loading step is performed using an aqueous mixture which comprises from about 25 to about 35 percent by volume of a solution comprising a water miscible organic modifier. In particular aspects, the water miscible organic modifier is hexylene glycol.

Following the loading of the insulin or insulin analogue onto the column, the column is washed in a step-wise fashion with a first wash solution comprising a concentration of mineral salt of about 10 to 20 mM for at least four or five column volumes up to about 20 column volumes. The first wash may be followed by an optional step of washing the column with a second wash solution comprising a mineral salt at a concentration that is greater than the mineral salt concentration in the first wash solution and less than a mineral salt concentration capable of eluting the insulin or insulin analogue from the column prior to eluting the insulin or insulin analogue for at least 15 to 20 column volumes. Elution of the insulin or insulin analogue is achieved by applying to the column an elution solution comprising a concentration of mineral salt capable of eluting the insulin or insulin analogue from the column for at least 10 column volumes or for a time until the amount of insulin or insulin analogue detected by UV monitoring in a fraction during the elution is about 10% of the peak fraction of insulin or insulin analogue during the elution as determined by UV monitoring. Yield may be monitored by measuring UV absorbance of fractions collected during the elution and purity may be determined by HPLC. The mineral salt may be NaCl.

In a further aspect, following the loading of the insulin or insulin analogue onto the column, the column is washed in a step-wise fashion with a first wash solution comprising about 18 to 22 mM of a mineral salt for at least five to 10 column volumes, which may be followed by an optional second wash with a second wash solution comprising about 35 to 39 mM of a mineral salt for at least 10 column volumes. Elution of the insulin or insulin analogue is achieved by applying to the column an elution solution comprising about 80 to 100 mM of a mineral salt for at least 10 column volumes or for a time until the amount of insulin or insulin analogue detected by UV monitoring in a fraction during the elution is about 10% of the peak fraction of insulin or insulin analogue during the elution as determined by UV monitoring. Yield may be monitored by measuring UV absorbance of fractions collected during the elution and purity may be determined by HPLC. The mineral salt may be NaCl.

In a further aspect, following the loading of the insulin or insulin analogue onto the column, the column is washed in a step-wise fashion with a first wash solution comprising about 18 to 22 mM of a mineral salt for about 18 to 20 column volumes, which may followed by an optional second wash with a second wash solution comprising about 35 to 39 mM of a mineral salt for about 18 to 20 column volumes. Elution of the insulin or insulin analogue is achieved by applying to the column an elution solution comprising about 80 to 100 mM of a mineral salt for 18 to 20 column volumes or for a time until the amount of insulin or insulin analogue detected by UV monitoring in a fraction during the elution is about 10% of the peak fraction of insulin or insulin analogue during the elution as determined by UV monitoring. Yield may be monitored by measuring UV absorbance of fractions collected during the elution and purity may be determined by HPLC. The mineral salt may be NaCl.

In a further aspect, following the loading of the insulin or insulin analogue onto the column, the column is washed in a step-wise fashion with a first wash solution comprising about 18 to 22 mM of a mineral salt for at least five to 10 column volumes, which may be followed by an optional second wash with a second wash solution comprising about 35 to 39 mM of a mineral salt for at least 10 column volumes. Elution of the insulin or insulin analogue is achieved by applying to the column an elution solution comprising about 93 to 97 mM of a mineral salt for at least 10 column volumes or for a time until the amount of insulin or insulin analogue detected by UV monitoring in a fraction during the elution is about 10% of the peak fraction of insulin or insulin analogue during the elution as determined by UV monitoring. Yield may be monitored by measuring UV absorbance of fractions collected during the elution and purity may be determined by HPLC. The mineral salt may be NaCl.

In a further aspect, following the loading of the insulin or insulin analogue onto the column, the column is washed in a step-wise fashion with a first wash solution comprising about 18 to 22 mM of a mineral salt for about 18 to 20 column volumes, which may followed by an optional second wash with a second wash solution comprising about 35 to 39 mM of a mineral salt for about 18 to 20 column volumes. Elution of the insulin or insulin analogue is achieved by applying to the column an elution solution comprising about 93 to 97 mM of a mineral salt for 18 to 20 column volumes or for a time until the amount of insulin or insulin analogue detected by UV monitoring in a fraction during the elution is about 10% of the peak fraction of insulin or insulin analogue during the elution as determined by UV monitoring. Yield may be monitored by measuring UV absorbance of fractions collected during the elution and purity may be determined by HPLC. The mineral salt may be NaCl.

In a further aspect, following the loading of the insulin or insulin analogue onto the column, the column is washed in a step-wise fashion with a first wash solution comprising 20 mM±2.5 mM of a mineral salt for about 18 to 20 column volumes, which may optionally be followed by a second wash with a second wash solution comprising 37 mM±2.5 mM of a mineral salt for about 18 to 20 column volumes. Elution of the insulin or insulin analogue is achieved by applying to the column an elution solution comprising 95 mM±2.5 mM of a mineral salt for 18 to 20 column volumes or for a time until the amount of insulin or insulin analogue detected by UV monitoring in a fraction during the elution is about 10% of the peak fraction of insulin or insulin analogue during the elution as determined by UV monitoring. Yield may be monitored by measuring UV absorbance of fractions collected during the elution and purity may be determined by HPLC. The mineral salt may be NaCl.

The temperature during the chromatography and elution is greater than 20° C. or 30° C. or greater than 40° C. In particular embodiments, the temperature during the chromatography and elution may be about 25° C. to about 50° C. or from about 37° C. to about 47° C. In particular embodiments, the temperature during the chromatography and elution is greater than greater than 40° C. In particular aspects, the temperature during the chromatography and elution is about 42° C. or more or about 42° C. to about 47° C. In particular aspects, the temperature during the chromatography and elution is about 42° C. or at least 42° C. Preferably, the temperature is kept constant or nearly constant over the course of the chromatography and elution. The operating pressure during the chromatography and elution is substantially constant. The chromatography and elution may be carried out using a column differential pressure that is less than 1.1 MPa, less than 0.5 MPa, or about 0.276 MPa. The eluent flow rates may be from about 182 to about 201 cm/hour.

In another aspect, the elution may be performed with a mineral salt gradient over time, for example, by a low mineral salt concentration being present in the elution buffer at the start of the elution (which initially can be zero percent salt) and by increasing the mineral salt concentration during the elution process. In particular aspects, the mineral salt may be NaCl. The operating temperature and pressure during the chromatography is substantially constant. The chromatography may be carried out using a column differential pressure that is less than 1.1 MPa, less than 0.5 MPa, or about 0.276 MPa and at a temperature of about 25° to about 50° C., or of about 38° to about 50° C., or of about or at least 42° C. or more, or of about 42° to about 47° C., or of about 42° C., or at least 42° C. Yield may be monitored by measuring UV absorbance and purity may be determined by HPLC. In particular aspects, the first wash solution, the optional second wash solution, and the elution solution, each comprises from 10 to about 50 percent by volume of a water miscible organic modifier. In a further aspect, the loading step is performed using an aqueous mixture which comprises from about 25 to about 35 percent by volume of a water miscible organic modifier. In particular aspects, the water miscible organic modifier is hexylene glycol.

In further aspects of the process disclosed herein, the first and second wash steps and the eluting steps are performed using a first, second, and eluting solution, each comprising an aqueous mixture having about 25 to about 35 percent by volume of a water miscible organic modifier, which in a further aspect, the first and second wash steps and the eluting step are performed using an aqueous mixture which comprises from about 30 percent by volume of a water miscible organic modifier. In a further aspect of the process, the water miscible organic modifier is hexylene glycol.

Concentrating the insulin or insulin analogue from the eluates obtained from the elution may be achieved by precipitation with zinc salt or by crystallization using methods known in the art. The resulting insulin precipitates may be isolated by decantation, centrifugation, or filtration, and then dried. The present invention is suitable not only for analytical chromatography but also for preparative chromatography, in particular when the process according to the invention is carried out with a preparative high-pressure liquid chromatography (HPLC) system. Thus, the present invention may be used in a process for preparing insulin or insulin analogue for use in treating diabetes.

The following examples are intended to promote a further understanding of the present invention.

EXAMPLE 1

The acidic cation exchange (CEX) column is packed with BioSepra CM Ceramic HyperD F, a high-capacity hydrogel polymerized within the pores of a rigid ceramic bead available from Pall Corporation, Port Washington, N.Y.; Cat. No. 20050. The defined volume of cation exchange material is first allowed to settle. The storage solution (20% ethanol) is decanted and replaced with an equal volume of CEX Strip/Storage Solution (Table 1) and the cation exchange material is resuspended in this solution. Settling, decanting, and resuspension with an equal volume of CEX Strip/Storage Solution are repeated two more times allowing for the sufficient equilibration of the cation exchange material with 30% hexylene glycol.

Next, the slurry is diluted to achieve a slurry percent of about 50% and held in the CEX Strip/Storage Solution for 24 hours. The cation exchange material slurry is transferred to the column and resuspended with a paddle. The upper head plate is inserted into the column and lowered to the solution interface. The column is flow-packed with CEX Strip/Storage Solution at a flow rate that produces a column differential pressure of about 40 psid (0.276 MPA) or more and at a temperature of about 20±2° C. Once a stable bed height is achieved, the flow rate is reduced and the upper head plate is lowered until about 2 to 3 mm above the cation exchange material interface. The head space is to prevent the cation exchange material from interfering with the sealing of the head plate. The column is returned to the packing pressure, and the bed is allowed to compress again. The procedure of slowing flow and lowering the head plate is repeated as necessary until the upper head plate is about 2 to 3 mm above the resin cation exchange material interface at the packing pressure.

Next, the column is connected to the chromatography skid and flushed with CEX Cleaning Solution (Table 1) as a pre-use sanitization, during which a final compression of the bed is observed. If necessary, the head plate should be lowered again to remain 2 to 3 mm above the cation exchange material interface.

Next, the column is promptly flushed with CEX Pre-Equilibration Solution (Table 1) and CEX Strip/Storage Solution.

TABLE 1

| CEX Chromatography Buffers & Raw Materials | | |
|---|---|---|
| Buffers/Raw Material | Description | Quantity |
| CEX Chromatography cation exchange material | BioSepra CM Ceramic HyperD F | 4.5 L/column pack |
| CEX Load Diluent | Hexylene Glycol | 14 kg/lot |
| CEX Pre-Equilibration Solution | 1M sodium acetate, pH 5.1 | 35 L/lot + 12 L/column pack |
| CEX Equilibration/ Wash 1 Solution (A1) | 20 mM sodium acetate, 20 mM sodium chloride, 30% hexylene glycol (v/v), pH 5.1 (before hexylene glycol addition) | 700 L/lot + 40 L/column pack |
| CEX Strip/Storage Solution (B1) | 20 mM sodium acetate, 250 mM sodium chloride, 30% hexylene glycol (v/v), pH 5.1 (before hexylene glycol addition) | 200 L/lot + 100 L/column pack |

TABLE 1-continued

CEX Chromatography Buffers & Raw Materials

| Buffers/Raw Material | Description | Quantity |
|---|---|---|
| CEX Cleaning Solution | 0.5N sodium hydroxide | 60 L/lot + 20 L/column pack |
| CEX Load Filter | Sartopore 2 (0.45/0.2 µm) MaxiCap Size 1 (0.6 m²) | 1/lot |

Next, the column is equilibrated with CEX Equilibration/Wash 1 Solution (Table 1) using a gradient initially to transition from the CEX Strip/Storage Solution to the CEX Equilibration/Wash 1 Solution at column differential pressure of about 40 psid (0.276 MPa) or less with an outlet temperature of about 40±2° C. Next, the column is flushed with the defined volume of CEX Strip/Storage Solution and the (low-to-high) transition is monitored via conductivity. Finally, the column may be stored until use.

Crude recombinant insulin or insulin analogue heterodimer obtained from a trypsin digest in 50 mM acetic acid, pH 3.5 is diluted to about 0.3 to 0.4 g/L with hexylene glycol prior to loading on the column and the pH adjusted to about 4.2. The mass of hexylene glycol to crude recombinant insulin is about 0.395 kg hexylene glycol/kg crude recombinant insulin. To prepare for loading of the diluted crude recombinant insulin, the column is equilibrated with CEX Equilibration/Wash 1 Solution using a gradient initially to transition from the CEX Strip/Storage Solution to the CEX Equilibration/Wash 1 Solution to prevent extreme pH excursions across the cation exchange material in the column. The column is loaded with the diluted crude recombinant insulin or insulin analogue at about 3-6 g insulin or insulin analogue/L cation exchange material/cycle. All steps between and including column wash and column strip use CEX Equilibration/Wash 1 Solution (A1) and CEX Strip/Storage Solution (B1) (Table 1). Following loading, the column is washed with CEX Equilibration/Wash 1 Solution containing about 20 mM NaCl.

Figure 1:
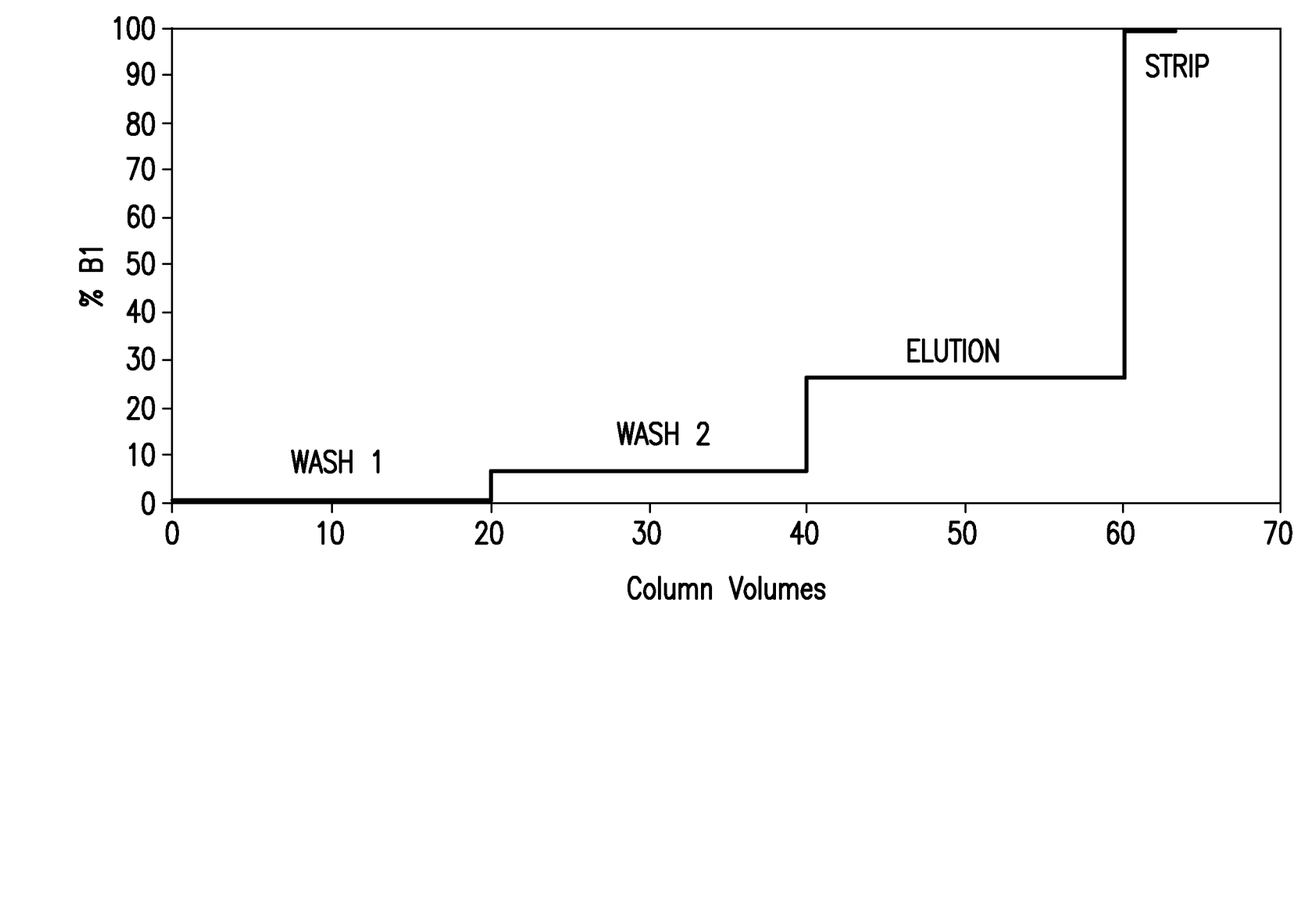

The column is operated a flow rate that produces a column differential pressure of about 40 psid (0.276 MPa) or less with an outlet temperature of about 42±2° C. In general, the flow rate is about 182 to 201 cm/hour or about 1 L/minute. The column is washed as shown in FIG. 1 with an A1/B1 mixture containing about 6.5±1.0% solution B1 in solution A1 to produce a solution comprising about 37 mM NaCl for about 18-20 column volumes. The column is then eluted as shown in FIG. 1 with an A1/B1 mixture containing about 26.1±1.0% B1 in A1 to produce a solution comprising about 95 mM NaCl with about 20 column volumes. During elution, fractions are collected during the elution process to allow analysis by UV absorption prior to pooling of those fractions that contain eluted insulin or insulin analogue. In general, collection of fractions begins at the start of the elution step and ends when the UV peak is below 10% of the peak maximum value. The fractions may be analyzed by HPLC to determine purity. The fractions that correspond to the required purity are combined. In general, purity as measured by HPLC is greater than 90% with a yield of about 60-85% or more.

EXAMPLE 2

A crude mixture of the acid-stable insulin analogue Gly (A21), Arg(B31), Arg(B32)-human insulin (insulin glargine) is purified as in Example 1. Because of non-specific enzymatic cleavages during the trypsin digest, very small amounts of product-related impurities, e.g. the three amino acid B-chain truncate (des-Thr) are produced. These product impurities, which are present in the crude mixture, are reduced using the method in Example 1. In general, the yield of the process has been about 65-85% with a purity of greater than 94% as determined by HPLC analysis.

Table of Sequences

| SEQ ID NO: | Description | Sequence |
|---|---|---|
| 1 | Human insulin A chain | GIVEQCCTSICSLYQLENYCN |
| 2 | Human insulin B chain | FVNQHLCGSHLVEALYLVCGERGFFYTPKT |
| 3 | Insulin glargine A chain | GIVEQCCTSICSLYQLENYCG |
| 4 | Insulin glargine B chain | FVNQHLCGSHLVEALYLVCGERGFFYTPKTRR |
| 5 | Insulin lispro B chain | FVNQHLCGSHLVEALYLVCGERGFFYTKPT |
| 6 | Insulin glusiline B chain | FVKQHLCGSHLVEALYLVCGERGFFYTPET |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A process for isolating an insulin glargine heterodimer from impurities produced by an enzymatic digest of a precursor insulin glargine to purify the insulin glargine heterodimer by chromatography comprising the steps of:
   (a) obtaining an acidic cation exchange column comprising an acidic cation exchange material comprising a high-capacity hydrogel polymerized within the pores of rigid ceramic beads and cross-linked to sulfo groups on the beads;
   (b) loading the column with a sample solution comprising about 30% (v/v) hexylene glycol and the insulin glargine heterodimer obtained from the enzymatic digest;
   (c) performing a chromatography that includes a step of washing the column with a first wash solution comprising a concentration of NaCl of about 20 mM followed by a step of washing the column with a second wash solution comprising NaCl at a concentration of about 37 mM wherein the first wash solution and the second wash solution each comprise about 30% (v/v) hexylene glycol; and
   (d) eluting the insulin glargine heterodimer from the column with an eluting solution comprising about 30% (v/v) hexylene glycol and a concentration of NaCl of about 95 mM;
   the process being performed under a column differential pressure of about 0.276 MPa and at an outlet temperature of about 42° C.

2. The process of claim 1, wherein the sample solution comprises from about 3.0 to about 26.0 g of protein per liter of acidic cation exchange material.

* * * * *

SEQUENCE LISTING

<160> NUMBER OF SEQ ID NOS: 6

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

```
<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 21
<212> TYPE: PRT
<213> ORGANISM: Artificial Sequence
<220> FEATURE:
<223> OTHER INFORMATION: Insulin glargine A chain

<400> SEQUENCE: 3

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 4
<211> LENGTH: 32
<212> TYPE: PRT
<213> ORGANISM: Artificial Sequence
<220> FEATURE:
<223> OTHER INFORMATION: Insulin glargine B chain

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Insulin lispro B chain

<400> SEQUENCE: 5

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Insulin glulisine B chain

<400> SEQUENCE: 6

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Glu Thr
            20                  25                  30
```